United States Patent
Ikemoto

(10) Patent No.: US 9,394,298 B2
(45) Date of Patent: Jul. 19, 2016

(54) PYRROLOQUINOLINE QUINONE TETRAALKALI SALT AND CRYSTAL THEREOF, METHODS FOR PRODUCING THESE, AND COMPOSITION

(71) Applicant: Mitsubishi Gas Chemical Company, Inc., Chiyoda-ku (JP)

(72) Inventor: Kazuto Ikemoto, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 14/420,754

(22) PCT Filed: Aug. 14, 2013

(86) PCT No.: PCT/JP2013/071914
§ 371 (c)(1),
(2) Date: Feb. 10, 2015

(87) PCT Pub. No.: WO2014/027669
PCT Pub. Date: Feb. 20, 2014

(65) Prior Publication Data
US 2015/0203488 A1    Jul. 23, 2015

(30) Foreign Application Priority Data

Aug. 17, 2012  (JP) ................... 2012-181103
Nov. 22, 2012  (JP) ................... 2012-256485

(51) Int. Cl.
| C07D 471/04 | (2006.01) |
| A61K 31/375 | (2006.01) |
| A61K 8/49 | (2006.01) |
| A61Q 19/00 | (2006.01) |
| A23L 1/30 | (2006.01) |

(52) U.S. Cl.
CPC ............... *C07D 471/04* (2013.01); *A23L 1/30* (2013.01); *A61K 8/4926* (2013.01); *A61K 8/4973* (2013.01); *A61K 31/375* (2013.01); *A61Q 19/00* (2013.01); *A23V 2002/00* (2013.01)

(58) Field of Classification Search
CPC ............... C07D 471/04; A61K 31/375
USPC .............................. 546/84; 514/292
See application file for complete search history.

(56) References Cited

U.S. PATENT DOCUMENTS

| 2010/0261749 A1* | 10/2010 | Kamimura | C07D 471/04 514/292 |
| 2011/0313164 A1 | 12/2011 | Zhong et al. | |
| 2012/0116087 A1 | 5/2012 | Edahiro et al. | |
| 2012/0226045 A1 | 9/2012 | Ikemoto et al. | |
| 2013/0225632 A1 | 8/2013 | Ikemoto et al. | |
| 2013/0253001 A1 | 9/2013 | Ikemoto | |

FOREIGN PATENT DOCUMENTS

| WO | 2010 111934 | 10/2010 |
| WO | 2011 007633 | 1/2011 |
| WO | 2011 055796 | 5/2011 |
| WO | 2012 039474 | 3/2012 |
| WO | 2012 070649 | 5/2012 |

OTHER PUBLICATIONS

Toshimasa Ishida et al , J. Am. Chem. Soc. 1989, I I I , 6822-6828 Molecular and Crystal Structure of PQQ (Methoxatin ), a Novel Coenzyme of Quinoproteins: Extensive Stacking Character and Metal Ion Interaction.*
A new redox-cofactor vitamin for mammals, Brief Communications, 2003, Takaoki Kasakara et al.*
Urakami, T., et al., "Characteristics of Coenzyme PQQ Obtained from Culture Broth of Microorganism", Vitamins, vol. 67, No. 9, pp. 485-491, (1993) (with partial English translation).
Corey, E.J., et al., "Total Synthesis of the Quinonoid Alcohol Dehydrogenase Coenzyme (1) of Methylotrophic Bacteria", J. Am. Chem. Soc., vol. 103, pp. 5599-5600, (1981).
International Search Report Issued Nov. 19, 2013 in PCT/JP13/071914 Filed Aug. 14, 2013.

* cited by examiner

*Primary Examiner* — Rita Desai
(74) *Attorney, Agent, or Firm* — Oblon, McClelland, Maier & Neustadt, L.L.P.

(57) ABSTRACT

An object of the present invention is to provide a pyrroloquinoline quinone tetraalkali salt needing no special reagent, having a high solubility in a solvent, being capable of providing a high-concentration pyrroloquinoline quinone aqueous solution, being hardly changed in color even if being concurrently used with ascorbic acid, and being of a high quality and a high purity; a crystal of a pyrroloquinoline quinone tetrasodium salt; a composition; and a simple method for producing the pyrroloquinoline quinone tetraalkali salt.

The pyrroloquinoline quinone tetraalkali salt is represented by the formula (1):

[Formula 1]

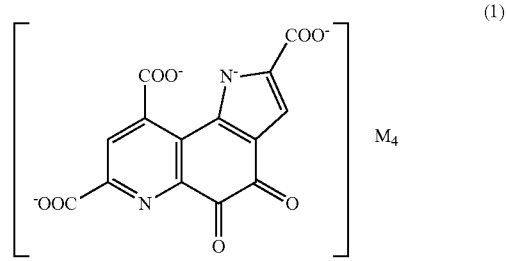

wherein M is each independently one selected from the group consisting of Li, K, Na, Rb and Cs.

13 Claims, 6 Drawing Sheets

Fig.2
(a)
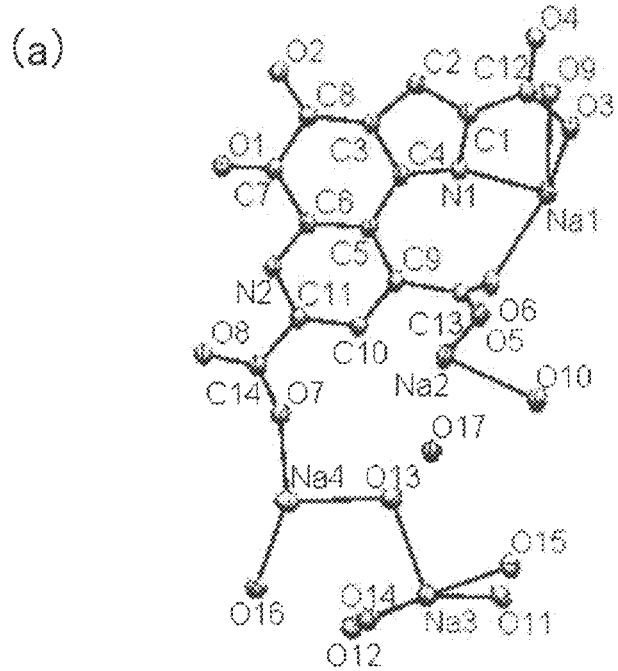
(b)
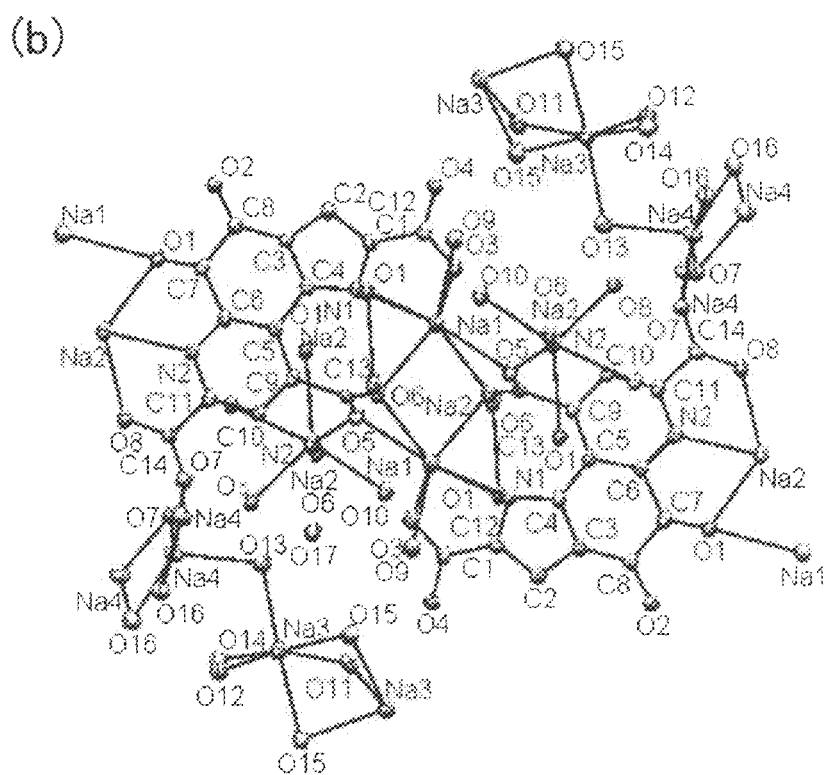

PYRROLOQUINOLINE QUINONE TETRAALKALI SALT AND CRYSTAL THEREOF, METHODS FOR PRODUCING THESE, AND COMPOSITION

CROSS-REFERENCE TO RELATED APPLICATIONS

This application is a National Stage of PCT/JP2013/071914 filed on Aug. 14, 2013. This application is based upon and claims the benefit of priority to Japanese Application No. 2012-181103, which was filed on Aug. 17, 2012, and to Japanese Application No. 2012-256485, which was filed on Nov. 22, 2012, the entire contents of which are incorporated herein by reference.

BACKGROUND OF THE INVENTION

1. Technical Field

The present invention relates to a pyrroloquinoline quinone tetraalkali salt and a crystal thereof, methods for producing these, and a composition.

2. Background Art

Pyrroloquinoline quinone is represented by the formula (2).

[Formula 1]

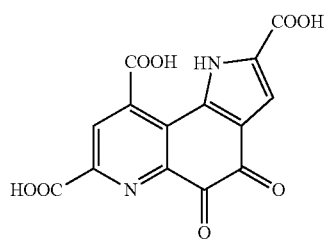

(2)

Pyrroloquinoline quinone (hereinafter, also referred to as "PQQ" or "free form") is known to have a possibility of having a function as a novel vitamin (coenzyme) and the like, and paid attention to as a useful substance for health supplements, cosmetics and the like. PQQ exists in fungi and yeasts of eukaryotes, not limited to bacteria, and carries out an important function as a coenzyme. PQQ further has been found so far to have many physiological activities including cell growth-stimulating action, anticataractous action, liver disease-preventing/treating action, injury-curing action, antiallergic action, reverse transcriptase-inhibiting action and glyoxalase I-inhibiting action-anticancer action.

Monoalkali salts, dialkali salts and trialkali salts in which 1 to 3 alkali metal ions are attached to pyrroloquinoline quinone have so far been known. Although the alkali salts of PQQ so far reported are known to be water-soluble substances, the solubility of the salts are actually low, and the solubility of their free form is even lower. An alkali salt whose structure has so far been determined as a crystal is a disodium salt (Non Patent Literature 1). A crystal polymorph of a disodium salt is similarly known (Patent Literature 1).

Since PQQ has so far been considered to be decomposed by alkalinity, the structure of crystallized substances thereof under the alkali condition has not been studied (Non Patent Literature 2)

CITATION LIST

Patent Literature

Patent Literature 1: International Publication No. WO2011/007633

Non Patent Literature

Non Patent Literature 1: JACS, Vol. 103, p. 5599-5600 (1981)
Non Patent Literature 2: Vitamin Vol. 67, No. 9, 1993

SUMMARY OF INVENTION

Technical Problem

As described above, since pyrroloquinoline quinone and its salts have a low solubility, it is difficult to make a high-concentration aqueous solution thereof. However, since the aqueous solution is most used when being provided for food and pharmaceutical fields, an aqueous solution in which PQQ is dissolved in a high concentration and does not deposit is demanded.

Further for separation and purification of PQQ, if the solubility of PQQ is low, such disadvantages arise that a large amount of a solvent (particularly water) becomes necessary in order to dissolve PQQ, which necessitates a large apparatus, and which makes the amount of waste liquid large.

Pyrroloquinoline quinone further has a problem of being liable to be changed in color by a reaction with ascorbic acid.

The present invention has been achieved in consideration of the above-mentioned problems, and an object thereof is to provide a pyrroloquinoline quinone tetraalkali salt needing no special reagent, having a high solubility in a solvent, being capable of providing a high-concentration pyrroloquinoline quinone aqueous solution, being hardly changed in color even if being concurrently used with ascorbic acid, and being of a high quality and a high purity; a crystal thereof; simple methods for producing these; and a composition.

Solution to Problem

As a result of exhaustive studies to solve the above-mentioned problems, the present inventors have found that the use of a salt of pyrroloquinoline quinone having a predetermined structure can solve the above-mentioned problems, and this finding has led to the completion of the present invention.

That is, the present invention is as follows.

[1]

A pyrroloquinoline quinone tetraalkali salt represented by the following formula (1):

[Formula 2]

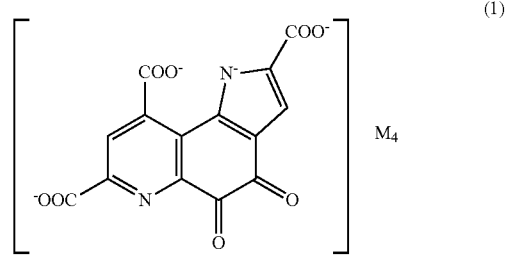

(1)

wherein M is each independently one selected from the group consisting of Li, K, Na, Rb and Cs.

[2]

A crystal comprising the pyrroloquinoline quinone tetraalkali salt according to the above [1].

[3]

The crystal according to the above [2], wherein at least one of M in the formula (1) is Na.

[4]

The crystal according to the above [2] or [3], wherein the crystal has peaks at 2θ in powder X-ray diffractometry using Cu-Kα observed at 5.89±0.4°, 11.72±0.4°, 12.43±0.4°, 13.59±0.4°, 18.09±0.4°, 23.93±0.4°, 26.50±0.4° and 29.40±0.4°.

[5]

The crystal according to any one of the above [2] to [4], wherein the crystal has the following dimensions as measured by a single crystal X-ray structural analysis:
Unit lattice dimensions
a=21.6072 (5) Å;
b=6.80401 (17) Å;
c=30.1070 (7) Å; and
V=4426.20 (18) Å$^3$.

[6]

A composition comprising:
the pyrroloquinoline quinone tetraalkali salt according to the above [1], and/or the crystal according to any one of the above [2] to [5]; and
ascorbic acid.

[7]

A method for producing a pyrroloquinoline quinone tetraalkali salt, comprising a mixing step of mixing a pyrroloquinoline quinone and/or a pyrroloquinoline quinone alkali salt, with an alkali metal compound under a strong alkaline condition.

[8]

The method for producing the pyrroloquinoline quinone tetraalkali salt according to the above [7], wherein the alkali metal compound is sodium hydroxide.

[9]

The method for producing the pyrroloquinoline quinone tetraalkali salt according to the above [7] or [8], wherein the strong alkaline condition in the mixing step is a pH of 10 to 14.

[10]

The method for producing the pyrroloquinoline quinone tetraalkali salt according to any one of the above [7] to [9], further comprising, after the mixing step, a deposition step of adding a poor solvent of the pyrroloquinoline quinone tetraalkali salt to be obtained.

[11]

A method for producing a crystal of a pyrroloquinoline quinone tetraalkali salt, comprising a mixing step of mixing pyrroloquinoline quinone and/or a pyrroloquinoline quinone alkali salt, with an alkali metal compound under a strong alkaline condition.

[12]

A food comprising the pyrroloquinoline quinone tetraalkali salt according to the above [1], the crystal according to any one of the above [2] to [5], and/or the composition according to the above [6].

[13]

A cosmetic comprising the pyrroloquinoline quinone tetraalkali salt according to the above [1], the crystal according to any one of the above [2] to [5], and/or the composition according to the above [6].

Advantageous Effects of Invention

The present invention can provide a pyrroloquinoline quinone tetraalkali salt having a high solubility in a solvent, being capable of providing a high-concentration pyrroloquinoline quinone aqueous solution, being hardly changed in color even if being concurrently used with ascorbic acid, and being of a high quality and a high purity; a crystal thereof; methods for producing these; and a composition.

BRIEF DESCRIPTION OF DRAWINGS

FIG. 2 shows a PQQ tetrasodium salt crystal composition structure (ORTEP) obtained in Example 1.

DESCRIPTION OF EMBODIMENT

Figure 1:
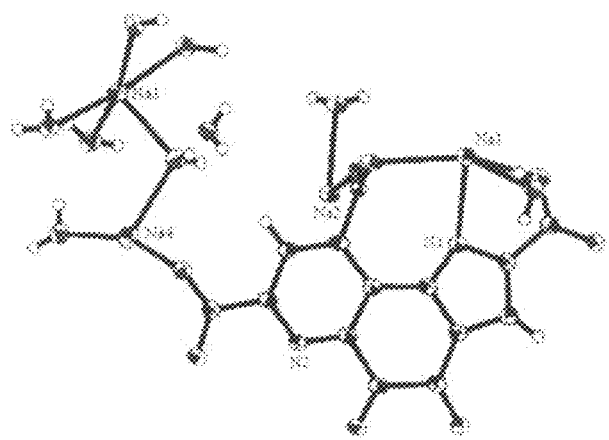
FIG. 1 shows a PQQ tetrasodium salt crystal composition structure (ORTEP) obtained in Example 1.

Hereinafter, an embodiment to carry out the present invention (hereinafter, referred to as "the present embodiment") will be described in detail, but the present invention is not limited thereto, and various modifications may be made without departing from its gist.

[Pyrroloquinoline Quinone Tetrasodium Salt]

A pyrroloquinoline quinone tetrasodium salt (hereinafter, also referred to as "PQQ tetraalkali salt") according to the present embodiment is represented by the formula (1).

[Formula 3]

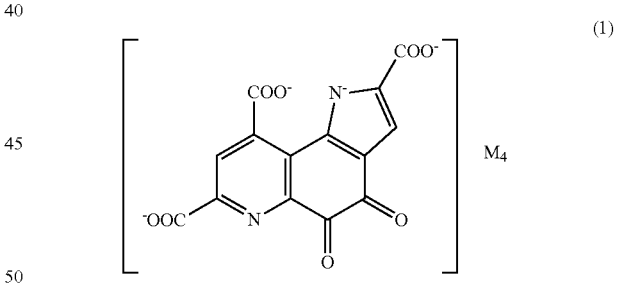

wherein M is each independently one selected from the group consisting of Li, K, Na, Rb and Cs.

The alkali metal M of the PQQ tetraalkali salt is each independently one selected from the group consisting of Li, K, Na, Rb and Cs. The kinds of the alkali metals M comprised in the PQQ tetraalkali salt may be one kind or two or more kinds. Among these, a PQQ tetraalkali salt having one kind of alkali metals is preferable. A PQQ tetraalkali salt in which the alkali metals are one kind is likely to be easily fabricated from a free form of PQQ. A PQQ tetraalkali salt comprising two or more kinds of alkali metals is also preferable. The PQQ tetraalkali salt comprising two or more kinds of alkali metals is not especially limited, but since for example, a disodium salt thereof is commercially available, so the raw material is easily available, a PQQ tetraalkali salt comprising sodium and other alkali metal ions is preferable.

A PQQ tetraalkali salt according to the present embodiment may comprise water, a solvent or an alkali metal compound as long as these are in 50% by mass or less in weight proportion.

[Crystal]

A crystal according to the present embodiment comprises the pyrroloquinoline quinone tetraalkali salt. Among those salts, a pyrroloquinoline quinone tetrasodium salt in which at least one M in the above formula (1) is Na is preferable, and a pyrroloquinoline quinone tetrasodium salt in which all M in the above formula (1) are Na is more preferable.

The pyrroloquinoline quinone tetraalkali salt is preferably a crystal from the viewpoint of the purity and the stability. Whether or not a pyrroloquinoline quinone tetraalkali salt is a crystal can be confirmed by a microscope, powder X-ray diffractometry (hereinafter, abbreviated to XRD in some cases), a single crystal X-ray analysis, electron beam diffraction and/or the like.

A crystal of a PQQ tetrasodium salt according to the present embodiment preferably has peaks at $2\theta$ in powder X-ray diffractometry using Cu-K$\alpha$ observed at 5.89±0.4°, 11.72±0.4°, 12.43±0.4°, 13.59±0.4°, 18.09±0.4°, 23.93±0.4°, 26.50±0.4° and 29.40±0.4°.

The measurement at the diffraction angles of $2\theta$ by powder X-ray diffractometry can be carried out, for example, under the following measurement condition. Alternatively, the measurement can also be carried out by a usual powder X-ray diffractometer installed with a monochromator.

(Measurement Condition)

Apparatus: RINT2500, manufactured by Rigaku Corp.
X-ray: Cu/tube voltage: 40 kV/tube current: 100 mA
Scanning speed: 4.000°/min
Sampling width: 0.020°

A crystal of a PQQ tetrasodium salt according to the present embodiment preferably has the following dimensions as measured by a single crystal X-ray structural analysis, for example:

Unit lattice dimensions
a=21.6072 (5) Å;
b=6.80401 (17) Å;
c=30.1070 (7) Å; and
V=4426.20 (18) Å$^3$.

The relative intensity of each peak in the single crystal X-ray structural analysis of the crystal of the PQQ tetrasodium salt according to the present embodiment can be represented by Table 1 according to the evaluation criteria of the following Table 2.

TABLE 1

| $2\theta$ (deg) | Relative Intensity |
|---|---|
| 5.89 ± 0.4° | vs |
| 11.72 ± 0.4° | vw |
| 12.43 ± 0.4° | vw |
| 13.59 ± 0.4° | vw |
| 18.09 ± 0.4° | vw~w |
| 23.93 ± 0.4° | vw |
| 26.50 ± 0.4° | vw~vs |
| 29.40 ± 0.4° | vw~w |

TABLE 2

| | Peak Intensities (%) to a Peak Having a Maximum Intensity (cps · deg) |
|---|---|
| vs | 50-100 |
| w | 25-50 |
| vw | 0-25 |

The relative intensity is calculated as a percentage to a peak having a maximum intensity.

[Methods for Producing a Pyrroloquinoline Quinone Tetraalkali Salt and a Crystal Thereof]

Methods for producing a PQQ tetraalkali salt and a crystal thereof according to the present embodiment comprise a mixing step of mixing a PQQ or a PQQ alkali salt (hereinafter, also collectively referred to as "PQQs") with an alkali metal compound under a strong alkaline condition. Here, the mixing step can be carried out in the presence of a solvent.

The mixing proportion of the PQQs and the alkali metal compound is preferably 3.5 to 10,000 mol of the alkali metal compound to 1 mol of the PQQs, more preferably 4 to 1,000 mol, and still more preferably 4 to 700 mol. When the mixing proportion is 3.5 mol or higher, the PQQs are likely to be more dissolved. When the mixing proportion is 10,000 mol or lower, the alkalinity does not become too high, which is likely to be practically excellent.

In the case of using a sodium compound as the alkali metal compound, the mixing proportion of PQQs and the sodium compound is preferably 3.5 to 100,000 mol of the sodium compound to 1 mol of the PQQs, more preferably 4 to 1,000 mol, and still more preferably 4 to 700 mol. When the mixing proportion is in the above range, a PQQ tetraalkali salt is likely to be more easily deposited.

After the mixing step, the salt or a crystal of the salt is deposited by reducing the solubility, and the solvent can thereafter be removed. A method for reducing the solubility specifically includes a method of removing a solvent by means of freeze-drying, vacuum drying, heat drying and/or the like at −20 to 200° C., and a method of depositing a salt or a crystal of the salt by adding a poor solvent. Particularly in the case of 4 sodium ions to 1 PQQ ion, the deposition is easy, therefore the case is preferable. A preferable mixing proportion may vary in some cases depending on the condition of reducing the solubility, that is, the deposition condition.

(PQQs)

PQQs usable are not especially limited, but examples thereof include a free form of PQQ, a monoalkali salt of PQQ, a dialkali salt of PQQ and a trialkali salt of PQQ. Such PQQs are not especially limited, but specifically include a salt of sodium, potassium, lithium, cesium or rubidium of PQQ, or an ammonium salt of PQQ. Among these, more preferable are a free form and a sodium or potassium salt of PQQ; and a sodium salt of PQQ, which is most easily available, is especially preferable. Here, the salt may be any of mono, di and tri type. Among these, preferable is a disodium salt. PQQs may be used singly or as a mixture of two or more. Among these, since a disodium salt is high in the stability, and has a higher solubility than a free form and a monoalkali salt, a PQQ tetraalkali salt is likely to be able to be more efficiently obtained.

These raw materials of the PQQs can be produced by an organic chemical synthesizing method, a fermenting method or the like. A salt of PQQ to be used as a raw material may be a crystal or amorphous. The salt may comprise impurities.

(Alkali Metal Compound)

An alkali metal compound to be used is not especially limited, but is, for example, lithium hydroxide, potassium hydroxide, sodium hydroxide, cesium hydroxide, rubidium hydroxide, lithium carbonate, potassium carbonate, sodium carbonate, cesium carbonate, rubidium carbonate, lithium bicarbonate, potassium bicarbonate, sodium bicarbonate, cesium bicarbonate, rubidium bicarbonate, lithium alkoxides, potassium alkoxides, sodium alkoxides, cesium alkoxides and rubidium alkoxides. Among these, more preferable is sodium hydroxide. A PQQ tetrasodium salt composed of sodium ions, which are nontoxic, is likely to be able to be more efficiently obtained by using sodium hydroxide, which is inexpensive.

A solvent usable in the mixing step is not especially limited, but examples thereof include water, methanol, ethanol, 2-propanol, butanol, glycerol, propylene glycol, ethylene glycol, polyethylene glycol, dioxane, dimethyl sulfoxide, dimethylacetamide, dipropylene glycol, methoxypropylene glycol, methoxyethylene glycol, methoxydipropylene glycol and methoxydiethylene glycol. Among these, water, or a mixed solvent of water with another solvent is preferable.

The strong alkaline condition in the mixing step is preferably a pH of 10 to 14, more preferably a pH of 12 to 14, and still more preferably a pH of 13 to 14. The pH is a measure, and a preferable pH may vary by an influence of a coexisting salt and the like in some cases. A method of regulating pH is not especially limited, but examples thereof include adding an acid or an alkali to a solution in the mixing step. The acid or alkali is not especially limited, but either of an organic one or an inorganic one can be used.

The alkali is not especially limited, but examples thereof include potassium hydroxide, lithium hydroxide, cesium hydroxide, rubidium hydroxide, sodium hydroxide, potassium carbonate, lithium carbonate, cesium carbonate, rubidium carbonate, sodium carbonate, potassium hydrogencarbonate, lithium hydrogencarbonate, cesium hydrogencarbonate, rubidium hydrogencarbonate, sodium hydrogencarbonate, choline and tetramethylammonium hydroxide.

The acid is not especially limited, but examples thereof include phosphoric acid, boric acid, hydrochloric acid, sulfuric acid, nitric acid, acetic acid and citric acid.

The reaction temperature when the formation of a salt is carried out in a solvent is not especially limited, but is preferably −20 to 140° C., more preferably −10 to 90° C., and still more preferably 0 to 70° C. The time necessary when the formation of a salt is carried out in a solvent is, though depending on the mixing speed, the stirring, the temperature, the concentration and the like, preferably 10 min to 7 days, more preferably 30 min to 5 days, and still more preferably 1 hour to 3 days. As the addition of an alkali metal compound such as of sodium to PQQs progresses to thereby increase the addition number of the alkali metal, the solubility of an obtained PQQ alkali salt in water is improved.

A PQQ tetraalkali salt formed in water or an organic solvent is subjected to drying, concentration, temperature reduction, poor solvent addition, salting out or pH change to thereby be deposited or otherwise. Among these, after the mixing step, a deposition step is preferably further included which adds a poor solvent of an obtained PQQ tetraalkali salt. The poor solvent needs to be selected according to a solvent used in the mixing step.

The poor solvent is not especially limited, but for example, a water-soluble organic solvent can be used. The water-soluble organic solvent is not especially limited, but specifically includes methanol, ethanol, 2-propanol, butanol, glycerol, propylene glycol, ethylene glycol, polyethylene glycol, dioxane, dimethyl sulfoxide, dimethylacetamide, dipropylene glycol, methoxypropylene glycol, methoxyethylene glycol, methoxydipropylene glycol and methoxydiethylene glycol. Among these, preferable is alcohols. By adding a water-soluble organic solvent as a poor solvent to a PQQ tetraalkali salt in the state dissolved in a solvent, the solubility of the PQQ tetraalkali salt is decreased to be thereby able to deposit the salt or a crystal of the salt.

A PQQ tetraalkali salt can also be fabricated by bringing PQQs into contact with a sodium compound and adding a solvent (poor solvent) hardly dissolving the PQQs to a solvent in which the PQQs are dissolved to thereby reduce the solubility.

Hereinafter, a preferable specific method for producing a PQQ tetrasodium salt as an example of a salt easily available and having a high solubility will be described.

A PQQ disodium salt is dissolved in water. The pH in the raw material dissolution is not especially limited. Easily usable is desirably a pH of 3 to 14, and more preferably a pH of 5 to 13. The pH regulation may be carried out by adding an alkaline sodium compound solution. The temperature at this time may be 0 to 140° C.; a sodium compound is added to this solution; and then by making the pH to be 10 or higher, a 4-sodium salt can be prepared. The reaction time is not especially limited, but the reaction can be carried out in about 5 min to 1 week. In the case of a small scale, the reaction is completed in a short time, but in the case of a large scale, a long time is necessary. The temperature at this time may be −20 to 140° C., and is preferably 0 to 80° C. The reacted liquid is subjected to drying-up or recrystallization to be thereby able to obtain a salt as a solid. In the present embodiment, the salt is not necessarily a solid. A solvent in which the recrystallization is carried out may be water or an organic solvent. The obtained solid may be dried at normal pressure or reduced pressure.

Then, another preferable specific method for producing a PQQ tetrapotassium salt as an example of a salt easily available and having a high solubility will be described.

A PQQ free form is suspended in water. The temperature at this time may be 0 to 140° C.; a potassium hydroxide compound is added to this solution to be thereby able to prepare a tetrapotassium salt. The reaction time is not especially limited, but the reaction can be carried out in about 5 min to 1 week. In the case of a small scale, the reaction is completed in a short time, but in the case of a large scale, a long time is necessary. The temperature at this time may be −20 to 140° C., and is preferably 0 to 80° C. The reacted liquid is subjected to drying-up or recrystallization to be thereby able to obtain a salt as a solid. A solvent in which the recrystallization is carried out may be water or an organic solvent. The obtained solid may be dried at normal pressure or reduced pressure.

It does not matter even if PQQs as the raw material other than a PQQ tetraalkali salt as the target substance are mingled in the PQQ tetraalkali salt according to the present embodiment. When the PQQs as the raw material are comprised, the control of the solubility and the dissolution speed is likely to become easy. The mixing proportion of the PQQ tetraalkali salt and the PQQs can be designed according to the purpose. A easily usable mixing proportion of the PQQ tetraalkali salt and the PQQs is, in weight ratio, with respect to 1 of the PQQs, preferably 0.01 to 100 of the PQQ tetraalkali salt, more preferably 0.02 to 50 thereof, and still more preferably 0.05 to 20 thereof.

[Composition]

A composition according to the present embodiment comprises the above PQQ tetraalkali salt and/or a crystal of the above PQQ tetraalkali salt, and ascorbic acid.

The PQQ tetraalkali salt according to the present embodiment can be an effective component for pharmaceuticals for humans and animals, cosmetics, functional foods, animal feeds and the like. The salt can be provided in forms such as of skin external preparations, injections, oral preparations and suppositories, and forms such as of daily eaten foods and beverages, nutrient foods and various types of hospital foods. Here, examples of excipients used in preparation of liquids include water, saccharides such as fructose and glucose, oils such as peanut oil, soybean oil and olive oil, and glycols such as polyethylene glycol and polypropylene glycol. Examples of diluents for solid preparations such as tablets, capsules and granules include, but not limited to, saccharides such as lactose, sucrose and mannitol; lubricants such as kaolin, talc, and magnesium stearate; disintegrants such as starch and sodium alginate; binders such as polyvinyl alcohol, cellulose, and gelatin; surfactants such as fatty acid esters; and plasticizers such as glycerol. As required, a dissolution promoter, a filler and the like may be added.

It does not matter even if PQQs as the raw material are mingled in the composition of a PQQ tetraalkali salt according to the present embodiment. When the PQQs are mixed, the control of the solubility and the dissolution speed becomes easy. The mixing proportion of the PQQ tetraalkali salt and the PQQs can be designed according to the purpose. An easily usable mixing proportion of the PQQ tetraalkali salt and the PQQs is, in weight ratio, with respect to 1 of the PQQs, preferably 0.01 to 100 of the PQQ tetraalkali salt, more preferably 0.05 to 20 thereof, and still more preferably 0.1 to 10 thereof.

The composition of a PQQ tetraalkali salt according to the present embodiment may comprise a solvent or an alkali compound. The content of the solvent or the alkali compound is not especially limited, but is, in weight proportion, preferably 50% by mass or lower, more preferably 0 to 40% by mass, and still more preferably 0 to 30% by mass.

The PQQ tetraalkali salt according to the present embodiment may be used singly or in a combination with other materials. Examples of combinational materials include vitamins such as Coenzyme Q10, vitamin B, vitamin C (ascorbic acid) and vitamin E, amino acids, carotenoids such as astaxanthin, α-carotene and β-carotene, ω3 fatty acids such as docosahexaenoic acid and eicosapentaenoic acid, and ω6 fatty acids such as arachidonic acid, but examples thereof are not limited thereto.

Although particularly ascorbic acid is liable to be deteriorated if being brought into contact with water when being mixed, ascorbic acid is stable when being mixed with the PQQ tetraalkali salt according to the present embodiment. The mixing ratio of the PQQ tetraalkali salt and ascorbic acid is, in weight ratio, preferably 0.01 to 200 of ascorbic acid with respect to 1 of the PQQ tetraalkali salt. In a ratio lower than this range, the deterioration action is likely to become smaller.

Foods and cosmetics according to the present embodiment comprise the above pyrroloquinoline quinone tetraalkali salt, a crystal thereof and/or the above composition.

EXAMPLES

Hereinafter, the present invention will be described in more detail by way of Examples and Comparative Examples, but the present invention is not limited to these Examples.

Reagents to be used were ones manufactured by Wako Pure Chemical Industries, Ltd. unless otherwise specified.
(PQQ Analysis)

PQQ was identified using the following apparatus.
  Apparatus: a high performance liquid chromatography system, Lc-20A, manufactured by Shimadzu Corp.
  Column: YMC-Pack ODS-Tms (5 μm), 150×4.6 mm I.D.
  Measurement temperature: 40° C.
  Detection: absorbance at 260 nm
  Eluent: 100 mM $CH_3COOH$/100 mM $CH_3COONH_4$ (30/70, pH: 5.1)
  Elution rate: 1.5 mL/min
(Ion Chromatography)
  Cations of a PQQ alkali salt were analyzed by an ion chromatography system manufactured by Dionex Corp.
  Na ions were measured by a sodium ion meter manufactured by Horiba, Ltd.
(Measurement Condition of Powder X-Ray Diffractometry)
  Apparatus: RINT2500 manufactured by Rigaku Corp.
  X-ray: Cu/tube voltage: 40 kV/tube current: 100 mA
  Scanning speed: 4.000°/min
  Sampling width: 0.020°

Reference Example

Preparations of a PQQ Disodium Salt, a PQQ Trisodium Salt and a PQQ Free Form

PQQ as the raw material was obtained by the culture method of Japanese Patent No. 2692167. After the obtained PQQ was column-refined, sodium chloride was added thereto at a pH of 7 to thereby obtain a red solid. The solid was washed with a 50% ethanol to remove sodium chloride to thereby obtain a PQQ trisodium salt.

60 g of a solid of the hydrous PQQ trisodium salt comprising 20 g of PQQ was added to a mixed liquid of 500 mL of ion exchange water and 500 mL of ethanol. At this time, the solid had not been completely dissolved. Hydrochloric acid was added thereto at room temperature to thereby make the pH of the solution 3.5. The addition of hydrochloric acid was carried out dropwise slowly over about 2 hours. Thereafter, the mixture was stirred for 2 days. The mixture was filtered to thereby obtain a crystal of a hydrous PQQ disodium salt ($Na_2PQQ$) in a yield of 99% by mol.

3 g of the PQQ disodium was dissolved in 1 L of water; and hydrochloric acid was added to thereby make the pH of the solution 1. A red solid was deposited. The solid was filtered, washed with a 2N hydrochloric acid, and washed with water. The resultant was dried under reduced pressure to thereby obtain a PQQ free form in a yield of 85% by mol. The following experiments used these raw materials.

Example 1

A PQQ Tetrasodium Salt ($Na_4PQQ$)

[Fabrication of a Single Crystal]

500 μL, of a PQQ disodium-2 g/L aqueous solution and 100 μL of a 25% sodium hydroxide aqueous solution were mixed. At this time, the pH was 13.4. The solution was put in a 2-mL tube; 1,000 μL of methanol was slowly added to thereby make two layers. The solution was placed at room temperature, and then after 4 days, a red crystal was deposited. The crystal was taken out, and was subjected to a single crystal X-ray structural analysis using a single crystal X-ray structural analyzer (VariMax with RAPID system, manufactured by Rigaku Corp.) under the following condition.
  X-ray source: CuK (λ=1.54187 Å)
  Tube voltage: 40 kV
  Tube current: 30 mA
  Measurement temperature: −180° C. (using a spray low-temperature apparatus)
  Camera length: 127.4 mm
  Oscillation angle: 10°
  Exposure time: 200 sec/deg
  Total number of measurement sheets: 90 sheets (360 sheets×3 series)
  Total measurement time: 51 hours and 57 min (including the read and erase times)

Figure 3:
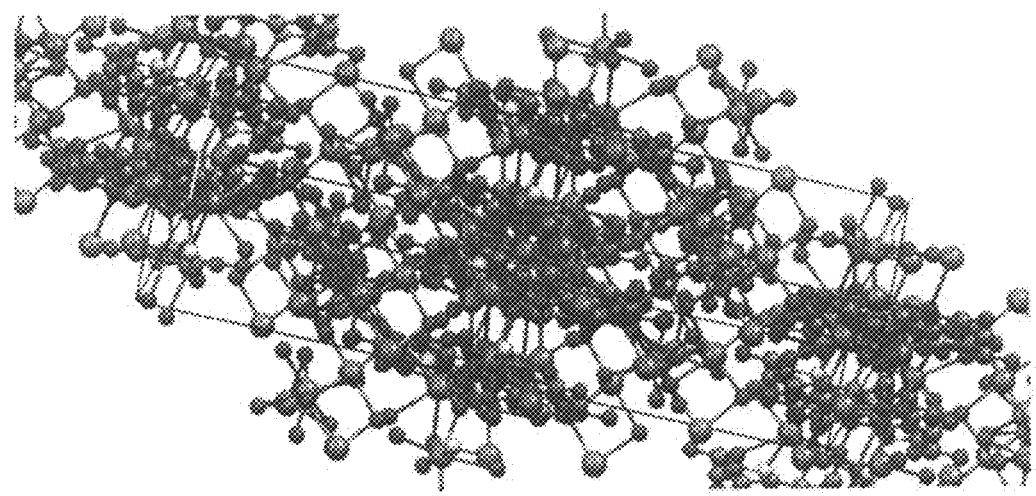
FIG. 3 shows a PQQ tetrasodium salt crystal composition structure obtained in Example 1.

A pyrroloquinoline quinone tetrasodium salt crystal composition structure is shown in FIG. 1 (ORTEP), FIG. 2 (ORTEP), FIG. 3 and Table 3. Further, single crystal parameters are shown in Table 4. FIG. 3 indicates that a crystal of four PQQ tetrasodium salts is present in one crystal lattice. FIG. 2(b) indicates an arrangement state of two PQQ tetrasodium salts in a crystal lattice; and FIG. 1 and FIG. 2(a) indicate only a structure of one PQQ tetrasodium salt comprised in a crystal lattice.

TABLE 3

| atom | x | y | z | Beq |
|---|---|---|---|---|
| Na1 | 0.47340(4) | 0.40014(13) | 0.44547(3) | 2.208(17) |
| Na2 | 0.40539(4) | 1.09238(12) | 0.53813(3) | 1.902(17) |
| Na3 | 0.42670(4) | 0.86812(12) | 0.74125(3) | 2.009(17) |
| Na4 | 0.26483(4) | 0.80080(13) | 0.69357(3) | 2.302(17) |
| O1 | 0.13304(6) | 0.6224(2) | 0.45767(5) | 2.08(3) |
| O2 | 0.17671(6) | 0.6649(2) | 0.37365(5) | 2.04(3) |
| O3 | 0.48807(6) | 0.6181(2) | 0.37715(5) | 2.11(3) |
| O4 | 0.43553(7) | 0.6147(2) | 0.31328(4) | 2.00(3) |

TABLE 3-continued

| atom | x | y | z | Beq |
|---|---|---|---|---|
| O5 | 0.43000(6) | 0.7591(2) | 0.52407(5) | 1.96(3) |
| O6 | 0.43124(6) | 0.4322(2) | 0.52108(5) | 1.90(3) |
| O7 | 0.23898(6) | 0.5584(2) | 0.64396(5) | 2.06(3) |
| O8 | 0.14795(6) | 0.5659(2) | 0.60869(4) | 2.11(3) |
| O9 | 0.45452(8) | 0.1685(3) | 0.38409(5) | 2.29(3) |
| O10 | 0.50955(7) | 1.1100(2) | 0.55647(6) | 2.13(3) |
| O11 | 0.5 | 0.6008(3) | 0.75 | 2.21(4) |
| O12 | 0.35333(7) | 0.6969(3) | 0.78893(5) | 2.15(3) |
| O13 | 0.37112(8) | 0.7709(3) | 0.67760(6) | 2.34(3) |
| O14 | 0.37415(7) | 1.1831(2) | 0.74563(6) | 2.37(3) |
| O15 | 0.51059(7) | 0.9859(3) | 0.69772(5) | 2.20(3) |
| O16 | 0.25148(8) | 1.0441(3) | 0.74714(5) | 2.36(3) |
| O17 | 0.39885(8) | 0.3682(3) | 0.66335(5) | 2.31(3) |
| N1 | 0.37931(7) | 0.6036(2) | 0.42633(5) | 1.65(3) |
| N2 | 0.20467(8) | 0.5923(2) | 0.52938(5) | 1.56(3) |
| C1 | 0.37922(9) | 0.6257(3) | 0.38041(6) | 1.70(3) |
| C2 | 0.32002(9) | 0.6522(3) | 0.36391(7) | 1.82(3) |
| C3 | 0.28048(9) | 0.6461(3) | 0.40107(6) | 1.69(3) |
| C4 | 0.31995(9) | 0.6168(3) | 0.43834(6) | 1.58(3) |
| C5 | 0.29715(9) | 0.6039(3) | 0.48387(6) | 1.59(3) |
| C6 | 0.23269(9) | 0.6050(3) | 0.49011(7) | 1.64(3) |
| C7 | 0.18868(9) | 0.6239(3) | 0.45160(7) | 1.69(3) |
| C8 | 0.21457(9) | 0.6494(3) | 0.40428(7) | 1.74(3) |
| C9 | 0.33381(9) | 0.5919(3) | 0.52243(7) | 1.62(3) |
| C10 | 0.30431(9) | 0.5774(3) | 0.56333(6) | 1.63(3) |
| C11 | 0.24035(9) | 0.5778(3) | 0.56579(7) | 1.67(3) |
| C12 | 0.43781(9) | 0.6186(3) | 0.35568(7) | 1.78(3) |
| C13 | 0.40399(9) | 0.5948(3) | 0.52176(6) | 1.65(3) |
| C14 | 0.20639(10) | 0.5667(3) | 0.60956(6) | 1.71(3) |

Atomic coordinate of a crystal of PQQ tetrasodium salt
Beq: Equivalence Isotropic Temperature Factors The crystal structure can also be confirmed by conversion of the powder X-ray diffractometry data. The data obtained using the single crystal was converted by using an X-ray structural analysis software, Mercury.

TABLE 4

A. Crystal Data

Empirical Formula C28H38N4Na8O33
Formula Weight 1142.53
Crystal Color, Habit brown, needle
Crystal Dimensions 0.530 X 0.020 X 0.020 mm
Crystal System orthorhombic
Lattice Type Primitive
Lattice Parameters a = 21.6072(5) Å
b = 6.80401(17) Å
c = 30.1070(7) Å
V = 4426.20(18) Å3
Space Group Pbcn (#60)
Z value 4
Dcalc 1.714 g/cm3
F000 2344.00
m(CuKa) 20.231 cm−1

B. Intensity Measurements

Diffractometer R-AXIS RAPID
Radiation CuKa (1 = 1.54187 Å)
multi-layer mirror monochromated
Voltage, Current 40 kV, 30 mA
Temperature 23.0° C.

This structure was a crystal comprising, in a unit lattice thereof, sodium in a proportion of 16 and water in a proportion of 34 with respect to 4 PQQ skeletons. That is, sodium is equivalent to 4 and water is equivalent to 8.5 to 1 PQQ skeleton. Hydrogen atoms of carboxylic acids and imidazole of the PQQ skeleton were withdrawn; and sodium was ionically bonded. It was found that the PQQ structure was not destroyed even under an alkali condition.

Example 2

Recrystallization by Methanol Addition 0.2 g of the PQQ disodium was added to 100 mL of water, and 40 g of a 25% sodium hydroxide aqueous solution was mixed therewith. The pH at this time was 13.5. 600 mL of methanol was added thereto, and placed at room temperature for 2 days to thereby deposit a red crystal. The solution was filtered, washed with 2-propanol, and dried under reduced pressure to thereby obtain 0.10 g of a red crystal. Example 2 revealed that the synthesis of the crystal of Example 1 could be carried out even if the scale of the synthesis was raised.

Example 3

Recrystallization by Ethanol Addition, Na/PQQ=4

Figure 4:
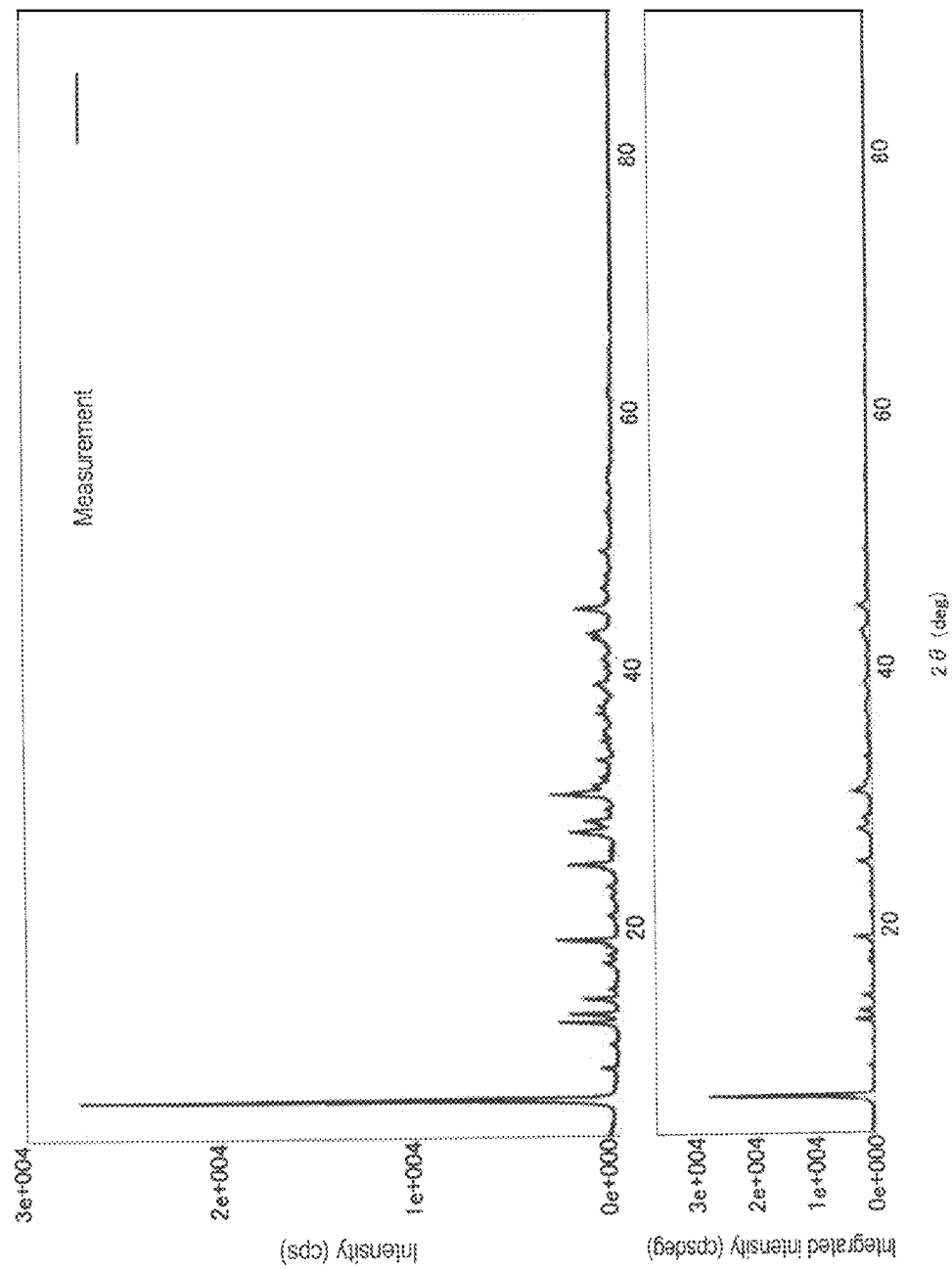
FIG. 4 shows a powder X-ray diffractometry result of a PQQ tetrasodium salt obtained in Example 3.

0.69 g of the PQQ disodium was added to 14 mL of water, and 16.9 g of a 25% sodium hydroxide aqueous solution was mixed therewith. The pH at this time was 13.5. 30 mL of ethanol was added thereto, and placed at room temperature for 1 day to thereby deposit a red crystal. The solution was filtered, washed with ethanol, and dried under reduced pressure to thereby obtain 0.98 g of a red crystal. The powder X-ray diffractometry result is shown in FIG. 4. As shown in FIG. 4, 2θ peaks were confirmed at 5.89°, 11.72°, 12.43°, 13.59°, 18.09°, 23.93°, 26.50°, 29.40° and 43.77°. The solid thus obtained was a crystalline substance. It was found from the peaks that the crystal obtained in Example 3 had nearly the same structure as the crystal of Example 1.

Example 4

Synthesis Using Evaporation, Na/PQQ=4

Figure 5:
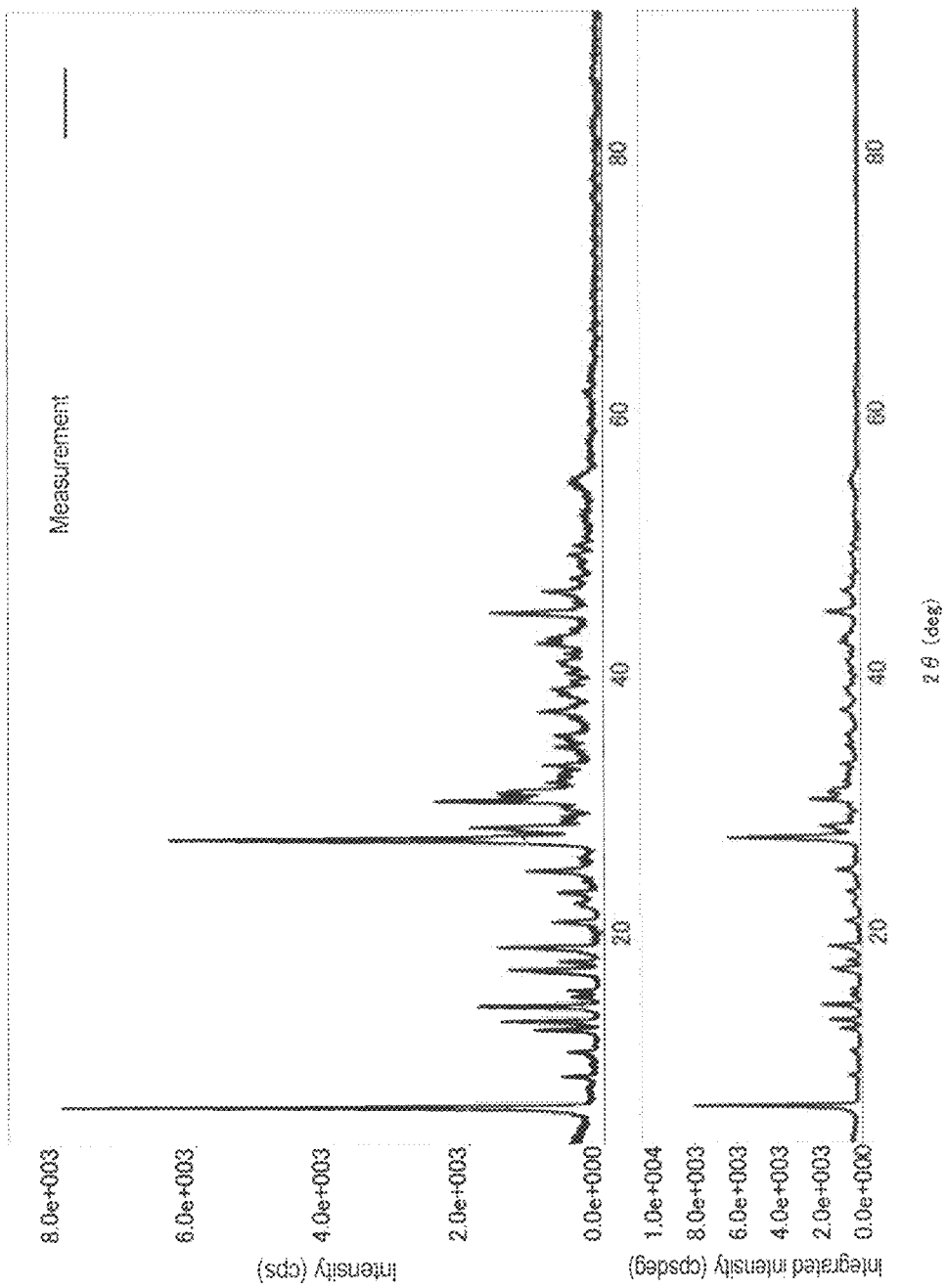
FIG. 5 shows a powder X-ray diffractometry result of a PQQ tetrasodium salt obtained in Example 4.

0.37 g of the PQQ disodium was added to 100 mL of water, and 0.32 g of a 25% sodium hydroxide aqueous solution was mixed therewith and stirred at room temperature for 1 hour. The pH at this time was 11. Thereafter, water was removed by evaporation using an evaporator to thereby obtain 0.41 g of a brown solid. The powder X-ray diffractometry result is shown in FIG. 5. As shown in FIG. 5, 2θ peaks were confirmed at 5.82°, 11.67°, 12.35°, 13.52°, 16.31°, 18.01°, 23.88°, 26.44°, 29.33°, 29.99° and 43.75°. The solid thus obtained was a crystalline substance. Although the color of the crystal was different, it was found from the peaks that the crystal obtained in Example 4 had nearly the same structure as the crystal of Example 1.

Example 5

A PQQ Tetralithium Salt (Li$_4$PQQ)

0.72 g of the PQQ free form was added to 50 mL of water. When 8 g of a lithium hydroxide aqueous solution prepared at 1 mol/kg was added thereto, the mixture turned from a suspension liquid to a homogeneous liquid. At this time, the pH of the solution was 11. The solution was put in a 300-mL eggplant flask, and water was completely blown off by an evaporator. The resultant was further dried by a reduced-pressure drier to thereby obtain 0.79 g of a black solid.

As a result of the calculation of Li/PQQ by using ion chromatography and liquid chromatography, the ratio was found to be 4. It was found from the liquid chromatography chart that the black solid had no decomposed substances and was stable even in the alkalinity. Lithium ions replaced protons of carboxylic acids and imidazole rings to thereby form the salt.

The black solid was found from XRD analysis to be a crystalline substance exhibiting 2θ peaks at 21.28°, 31.82°, 33.49°, 34.79° and 34.86°.

Example 6

A PQQ Disodium Dilithium Salt ($Li_2Na_2PQQ$)

0.38 g of the PQQ disodium was added to 50 mL of water. When 2 g of a lithium hydroxide aqueous solution prepared at 1 mol/kg was added thereto, the mixture turned from a suspension liquid to a homogeneous liquid. At this time, the pH of the solution was 11. The solution was put in a 300-mL eggplant flask, and water was completely blown off by an evaporator. The resultant was further dried by a reduced-pressure drier to thereby obtain 0.38 g of a dark-red solid.

As a result of the calculation of Li/PQQ and Na/PQQ by using ion chromatography and liquid chromatography, it was found that Li/PQQ was 2 and Na/PQQ was 2. It was found from the liquid chromatography chart that the dark-red solid had no decomposed substances and was stable even in the alkalinity.

The dark-red solid was found from XRD analysis to be a crystalline substance exhibiting 2θ peaks at 30.02°, 31.88°, 33.55° and 36.91°.

Example 7

A PQQ tetrapotassium salt ($K_4PQQ$)

0.72 g of the PQQ free form was added to 50 mL of water. When 8 g of a potassium hydroxide aqueous solution prepared at 1 mol/kg was added thereto, the mixture turned from a suspension liquid to a homogeneous liquid. At this time, the pH was 11. The solution was put in a 300-mL eggplant flask, and water was completely blown off by an evaporator. The resultant was further dried by a reduced-pressure drier to thereby obtain 0.89 g of a black solid.

As a result of the calculation of K/PQQ by using ion chromatography and liquid chromatography, the ratio was found to be 4. It was found from the liquid chromatography chart that the black solid had no decomposed substances and was stable even in the alkalinity.

The black solid was found from XRD analysis to be a crystalline substance exhibiting 2θ peaks at 24.49°, 26.11°, 27.38° and 28.04°.

Example 8

A PQQ tetrasodium salt ($Na_4PQQ$)/PQQ Trisodium Salt ($Na_3PQQ$)

0.75 g of the PQQ disodium was added to 50 mL of water, and 0.48 g of a 25-wt % sodium hydroxide was mixed therewith. The solution was put in a 300-mL eggplant flask, and water was completely blown off by an evaporator. The resultant was further dried by a reduced-pressure drier to thereby obtain 0.87 g of a solid.

As a result of the calculation of Na/PQQ by using ion chromatography and liquid chromatography, it was found that a tetrasodium salt and a trisodium salt coexisted. It was found from the liquid chromatography chart that the solid had no decomposed substances and was stable even in the alkalinity.

The solid was found from XRD analysis to be an amorphous substance exhibiting a small peak at 26.44° of 2θ.

Reference Example 1

Synthesis Using Evaporation, Na/PQQ=7

Figure 6:
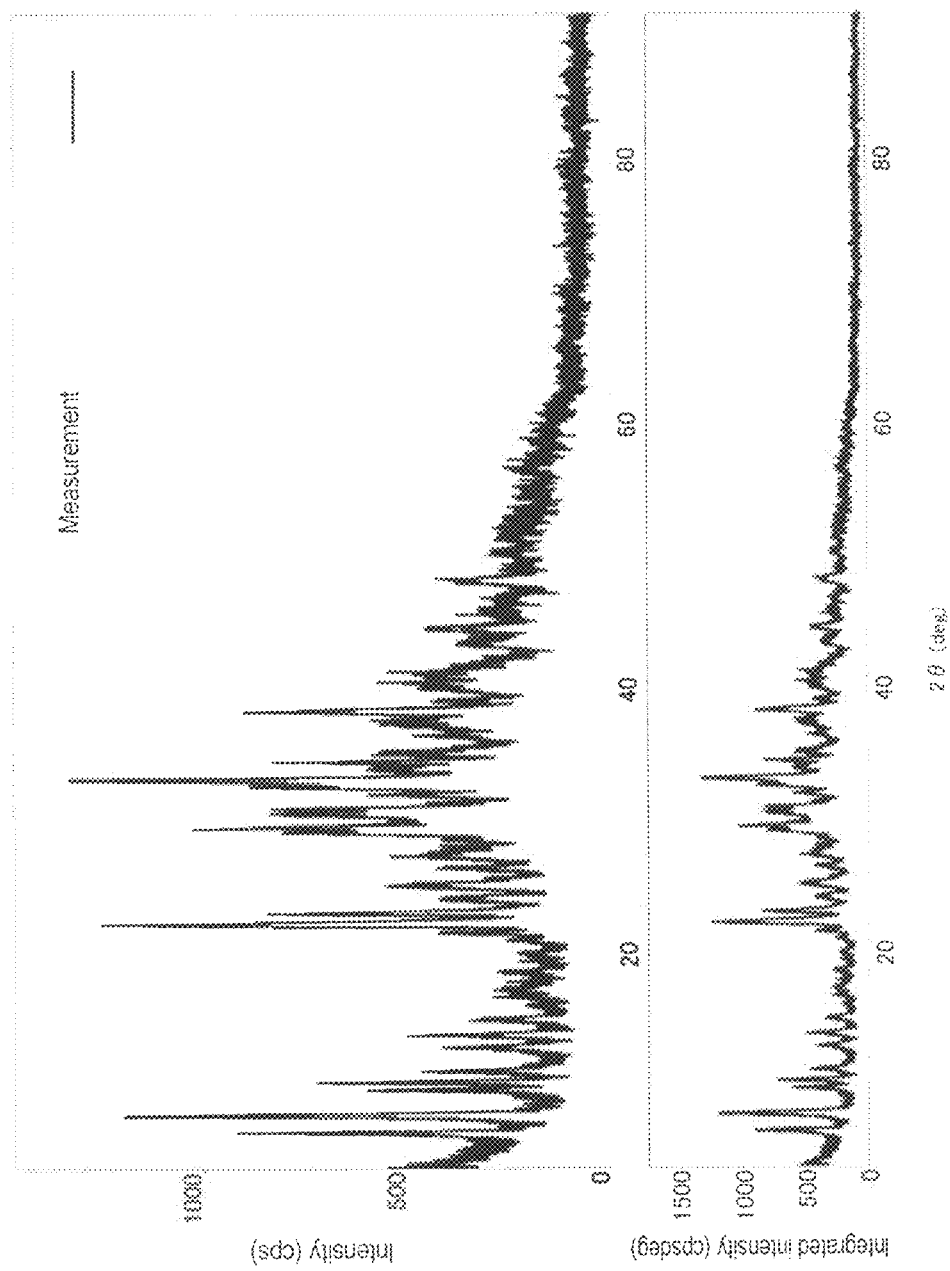
FIG. 6 shows a powder X-ray diffractometry result of a PQQ sodium salt obtained in Reference Example 1.

0.37 g of the PQQ disodium was added to 10 mL of water, and 0.80 g of a 25% sodium hydroxide aqueous solution was mixed therewith, and stirred at room temperature for 0.5 hours. Thereafter, the solvent was removed by an evaporator to thereby obtain 0.82 g of a yellowish green deposited solid. The powder X-ray diffractometry result is shown in FIG. 6. As shown in FIG. 6, many 2θ peaks were confirmed at 5.77°, 7.00°, 9.52°, 21.44°, 22.25°, 32.35°, 37.48° and many other angles. The solid obtained in Reference Example 1 was a crystalline substance. It was found from the peaks that the solid obtained in Reference Example 1 had a crystal structure different from the crystal of Example 1. It is conceivable that the solid obtained in Reference Example 1 was in a state that a PQQ tetrapotassium salt and excessive potassium hydroxide were present.

Reference Example 2

An Excessive-Potassium PQQ Tetrapotassium Salt ($K_5PQQ$)

0.72 g of the pyrroloquinoline quinone free form was added to 50 mL of water. When 10 g of a potassium hydroxide aqueous solution prepared at 1 mol/kg was added thereto, the mixture turned from a suspension liquid to a homogeneous liquid. The pH was 11.5. The solution was put in a 300-mL eggplant flask, and water was completely blown off by an evaporator. The resultant was further dried by a reduced-pressure drier to thereby obtain 1.04 g of a black solid.

As a result of the calculation of K/PQQ by using ion chromatography and liquid chromatography, the ratio was found to be 5. It was found from the liquid chromatography chart that the obtained solid had no decomposed substances and was stable even in the alkalinity. It is conceivable that the solid obtained in Reference Example 2 was in a state that a PQQ tetrapotassium salt and excessive potassium hydroxide were present. The solid exhibited a peak at 30.23° of 2θ in XRD analysis, but the peak intensity was weak and the solid was a low-crystallinity substance.

Comparative Example 1

A PQQ Disodium Salt ($Na_2PQQ$), and

Comparative Example 2

A PQQ Trisodium Salt ($Na_3PQQ$)

Comparative Example 1 and Comparative Example 2 used the PQQ disodium salt ($Na_2PQQ$) and the PQQ trisodium salt ($Na_3PQQ$) fabricated in Reference Examples, respectively.

[Test of the Reactivity with Ascorbic Acid]

Each PQQ salt shown in Table 5 was dissolved in water so as to become 1 g/L. 0.5 mL of a 100 g/L ascorbic acid aqueous solution was added to 1 mL of the solution, and its states after 2 hours, after 1 day and after 2 days were observed.

TABLE 5

| | | Test of the Reactivity with Ascorbic Acid | |
|---|---|---|---|
| | | after 2 hours | after 1 day |
| Example 1 | Na$_4$PQQ | red solution | red solution |
| Example 5 | Li$_4$PQQ | red solution | red solution |
| Example 6 | Li$_2$Na$_2$PQQ | red solution | red solution |
| Example 7 | K$_4$PQQ | red solution | red solution |
| Comp. Ex. 1 | Na$_2$PQQ | brown deposit | brown deposit |
| Comp. Ex. 2 | Na$_3$PQQ | brown deposit | brown deposit |
| Reference Ex. 2 | K$_5$PQQ | red solution | red solution |

It was found from comparison of Examples and Comparative Examples that the PQQ tetraalkali salts, when being mixed with ascorbic acid, exhibited no color change, formed no deposit and were stable. It was found in a long-term observation that a solution in which Na$_4$PQQ was dissolved and a solution in which K$_4$PQQ was dissolved hardly generated color change.

[Test of the Solubility]

50 mg of each PQQ salt shown in Table 6 was added to 0.5 mL of water so as to become supersaturated. Here, in the case where a PQQ salt was completely dissolved in this concentration, the amount of water was reduced. Thereafter, an ultrasonic wave was applied on the solution at room temperature of 23° C. The solution was subjected to a centrifugal separator; and the supernatant was subjected to a UV measurement by diluting it using a phosphoric acid buffer (pH: 7.4, manufactured by Gibco Corp.) so that the absorbance at 260 nm became in the range of 0 to 1. The solubility was calculated from the absorption. The UV measurement used a U-2000 spectrometer manufactured by Hitachi, Ltd. The results are shown in Table 6.

TABLE 6

| | | Test of the Solubility | |
|---|---|---|---|
| | | Solubility (mmol/L) | Solubility Ratio |
| Comp. Ex. 1 | Na$_2$PQQ | 7.99 | 1 |
| Comp. Ex. 2 | Na$_3$PQQ | 30.4 | 3.8 |
| Example 8 | Na$_3$PQQ + Na$_4$PQQ | 89.5 | 11.2 |
| Example 1 | Na$_4$PQQ | 463 | 58 |
| Example 5 | Li$_4$PQQ | 655 | 82 |
| Example 6 | Li$_2$Na$_2$PQQ | 89 | 11 |
| Example 7 | K$_4$PQQ | 84 | 10.5 |
| Reference Ex. 1 | Na$_7$PQQ | 119 | 14.9 |
| Reference Ex. 2 | K$_5$PQQ | 407 | 51 |

It was found from comparison of Examples and Comparative Examples that when PQQ had 4 cations, the solubility became very high, and the PQQ tetraalkali salts were easily dissolved. It was also found that the PQQ tetralithium salt was more easily dissolved than the PQQ tetrasodium salt.

[Test of the Dissolution Speed]

1 mg of each PQQ salt shown in Table 7 was added to an acryl-made absorbance measurement cell, and 2 mL of water was added thereto and the absorbance at 450 nm was measured. Here, the UV measurement used a U-2000 spectrometer manufactured by Hitachi, Ltd. The absorbance when every sample was dissolved and became homogeneous was taken to be 100, and the change with time thereof is shown in the following.

TABLE 7

| | | Test of the Dissolution Speed Absorbance | |
|---|---|---|---|
| | | After 1 min | After 30 min |
| Comp. Ex. 1 | Na$_2$PQQ | 41 | 48 |
| Example 1 | Na$_4$PQQ | 88 | 92 |
| Example 7 | K$_4$PQQ | 71 | 85 |
| Example 11 | Na$_2$PQQ (weight ratio: 1.0) Na$_4$PQQ (weight ratio: 0.5) | 61 | 71 |
| Reference Ex. 2 | K$_5$PQQ | 73 | 88 |

It was found from comparison of Examples and Comparative Examples that the PQQ tetrasodium salt had a higher dissolution speed than the PQQ disodium salt. It was also found that mixing the PQQ disodium salt and the PQQ tetrasodium salt could change the dissolution speed. It was found in the more detailed observation that the change in the amount of the mixture dissolved from after 1 min to after 30 min was larger than that of the case of using one kind of the salts, and making the salts to be a mixed salt could control the change with time of the amount of dissolution.

Comparative Example 3

Recrystallization by Ethanol at a pH of 3.1

2 g of the PQQ disodium was dissolved in 900 mL of water, and the pH was made at 3.1 by using hydrochloric acid. 900 mL of ethanol was added thereto, and placed for one night in a refrigerator. A red solid was deposited. As a result of an analysis of this solid by ion chromatography and liquid chromatography, Na/PQQ was 2, and the solid was a PQQ disodium salt. The recovery rate was 98%. At this pH, a PQQ tetrasodium salt could not be obtained.

Comparative Example 4

Recrystallization by Ethanol at a pH of 7.5

4 g of the PQQ disodium was dissolved in 900 mL of water, and the pH was made at 7.5 by using sodium hydroxide and phosphoric acid. 900 mL of ethanol was added thereto, and placed for one night in a refrigerator. A red solid was deposited. As a result of an analysis of this solid by ion chromatography and liquid chromatography, Na/PQQ was 3, and the solid was a PQQ disodium salt. The recovery rate was 95%. At this pH, a PQQ tetrasodium salt could not be obtained.

The present application is based on Japanese Patent Application (Japanese Patent Application No. 2012-181103), filed on Aug. 17, 2012 to the Japan Patent Office, and Japanese Patent Application (Japanese Patent Application No. 2012-256485), filed on Nov. 22, 2012 to the Japan Patent Office, the entire contents of which are hereby incorporated by reference.

INDUSTRIAL APPLICABILITY

The PQQ tetrasodium alkali salt according to the present invention has the industrial applicability in the fields of foods, pharmaceuticals, cosmetics, animal feeds and the like.

The invention claimed is:
1. A pyrroloquinoline quinone tetraalkali salt represented by the following formula (1):

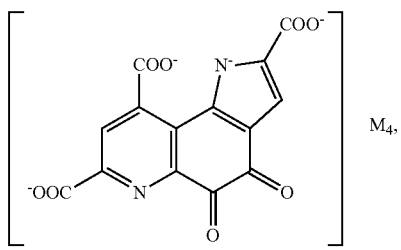

wherein each M is independently selected from the group consisting of Li, K, Na, Rb and Cs.

2. A crystal, comprising the pyrroloquinoline quinone tetraalkali salt according to claim 1.

3. The crystal according to claim 2, wherein at least one M in the formula (1) is Na.

4. The crystal according to claim 2, wherein the crystal has peaks at 2θ in powder X-ray diffractometry using Cu-Kα observed at 5.89±0.4°, 11.72±0.4°, 12.43±0.4°, 13.59±0.4°, 18.09±0.4°, 23.93±0.4°, 26.50±0.4° and 29.40±0.4°.

5. The crystal according to claim 2, wherein the crystal has the following dimensions as measured by a single crystal X-ray structural analysis:
Unit lattice dimensions
a=21.6072 (5) Å;
b=6.80401 (17) Å;
c=30.1070 (7) Å; and
V=4426.20 (18) Å$^3$.

6. A composition, comprising:
the pyrroloquinoline quinone tetraalkali salt according to claim 1; and
ascorbic acid.

7. A method for producing a pyrroloquinoline quinone tetraalkali salt, the method comprising mixing a pyrroloquinoline quinone, a pyrroloquinoline quinone alkali salt, or a mixture thereof, with an alkali metal compound under a strong alkaline condition.

8. The method according to claim 7, wherein the alkali metal compound is sodium hydroxide.

9. The method according to claim 7, wherein the mixing occurs at a pH of 10 to 14.

10. The method according to claim 7, further comprising, after the mixing step, adding a poor solvent to affect deposition of the pyrroloquinoline quinone tetraalkali salt.

11. A method for producing a crystal of a pyrroloquinoline quinone tetraalkali salt, the method comprising mixing a pyrroloquinoline quinone, a pyrroloquinoline quinone alkali salt, or a mixture thereof, with an alkali metal compound under a strong alkaline condition.

12. A food comprising the pyrroloquinoline quinone tetraalkali salt according to claim 1.

13. A cosmetic comprising the pyrroloquinoline quinone tetraalkali salt according to claim 1.

* * * * *